US00PP12737P2

(12) United States Plant Patent
Flora et al.

(10) Patent No.: US PP12,737 P2
(45) Date of Patent: Jul. 2, 2002

(54) ALMOND TREE NAMED 'BLUEGUM'

(75) Inventors: O. Hubert Flora; Jonathan J. Flora; Rodney D. Flora, all of Modesto, CA (US)

(73) Assignee: Driver Nursery, Inc., Modesto, CA (US)

( * ) Notice: Subject to any disclaimer, the term of this patent is extended or adjusted under 35 U.S.C. 154(b) by 0 days.

(21) Appl. No.: 09/575,212

(22) Filed: May 18, 2000

(51) Int. Cl.[7] ..... A01H 5/00
(52) U.S. Cl. ..... Plt./155
(58) Field of Search ..... Plt./155

*Primary Examiner*—Bruce R. Campell
*Assistant Examiner*—Annette H. Para
(74) *Attorney, Agent, or Firm*—Klarquist Sparkman, LLP

(57) ABSTRACT

An almond tree named 'Bluegum' that is an early season pollinator, which produces high quality, marketable crops.

5 Drawing Sheets

DESCRIPTION

The present invention relates to a new and distinct variety of almond tree (*Prunus Amygdalus*) that has been given the varietal name 'Bluegum.'

The original plant of the 'Bluegum' variety was discovered as a chance seedling of unknown parentage growing within a cultivated area of one of the inventor's farm located at 6201 Blue Gum Avenue, Modesto, Calif. During the non-bearing years of the seedling, the inventors protected it from the normal orchard practice of removing volunteer seedlings. As the original seedling tree reached reproductive maturity, the inventors noted its novel bloom date, excellent shell seal, and pleasant flavor and marked it for subsequent observation.

It is horticulturally understood that it is necessary to provide cross-pollination of almond trees since most commercially acceptable almond cultivars are not self-fertile. It is commonly acknowledged that the 'Nonpareil' variety (an unpatented well known variety of almond tree) of almond tree is a difficult variety to pollinate and produces more consistent crops when it has two pollinating varieties. Furthermore, the 'Nonpareil' variety performs best when its bloom dates are bracketed by two separate pollinator varieties. Both the original tree and the progeny trees of the 'Bluegum' variety have been observed to provide pollination on the early side of that combination. Additionally, the original tree of the 'Bluegum' variety has been shown to be a compatible with the later blooming pollinator variety known as 'Carmel' (U.S. Plant Pat. No. 2,641), and the progeny trees have been shown to be compatible with the later blooming pollinator variety known as 'Fritz' (U.S. Plant Pat. No. 3,005).

Equally important is almond nut quality and market acceptance. Almonds produced by the original tree of the 'Bluegum' variety are ripe for commercial harvesting just following almonds produced by the 'Nonpareil' variety but before almomds produced by the 'Carmel' variety, thereby providing harvest separation of plants if the different varieties are planted in adjoining rows. Almonds produced by the original tree of the 'Bluegum' variety are noteworthy in that they have a good shell seal thereby providing some natural insect protection. Additionally, the nut kernel of original tree of the 'Bluegum' variety is of high quality, providing excellent mild to sweet flavor and the nuts from the original tree have been found to fit into the commercially recognized "California" category.

More specifically, both the original tree and the progeny trees of the 'Bluegum' variety have been observed to bloom approximately 2 days earlier in the season than the 'Nonpareil' variety. Furthermore, nuts from the original tree have been observed to mature for harvesting approximately 10 days after the 'Nonpareil' variety, under the same environmental conditions prevailing in the San Joaquin Valley of Central California. The original tree and the progeny trees of the 'Bluegum' variety have been observed to produce nuts in volumes equal to, or greater than the 'Nonpareil' variety, while concurrently enhancing crops produced by the 'Nonpareil' variety. The original tree of the 'Bluegum' variety of almond tree also has a harvest date which is approximately 10 days ahead of the 'Carmel' variety of almond tree. The observations pertaining to nut flavor and characteristics are drawn from the original tree and are expected to carry over to the asexually propagated progeny.

ASEXUAL REPRODUCTION AND OBSERVATION OF THE NEW VARIETY

The first asexual reproduction of the newly discovered variety was performed by budding in 1998 at the direction of the inventors at Driver Nursery, Inc. in Modesto, Calif. Test trees resulting from this budding were planted in two geographically diverse test orchards in Modesto, Calif. and Kern County, Calif., respectively, for further observation. The flowering characteristics, pollination characteristics, and other characteristics of the new variety have been confirmed to exist in these two-year old asexually propagated progeny, except that mature harvestable nuts have yet to be collected from the progeny. The inventors have continually monitored the development of the progeny trees and expect that the nut characteristics of the asexually propagated progeny will be the same as those of the original tree of the 'Bluegum' variety.

Figure 1:
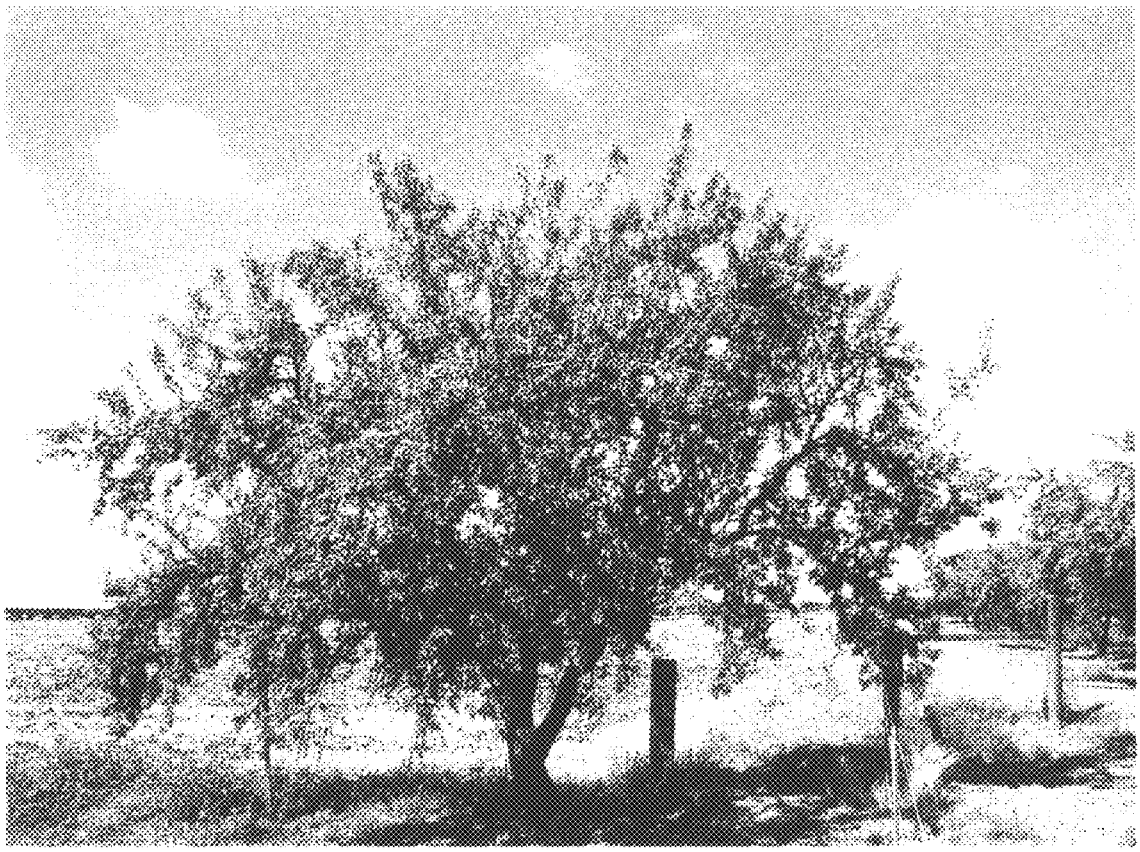
FIG. 1 is a picture of the original almond tree.
Figure 2:
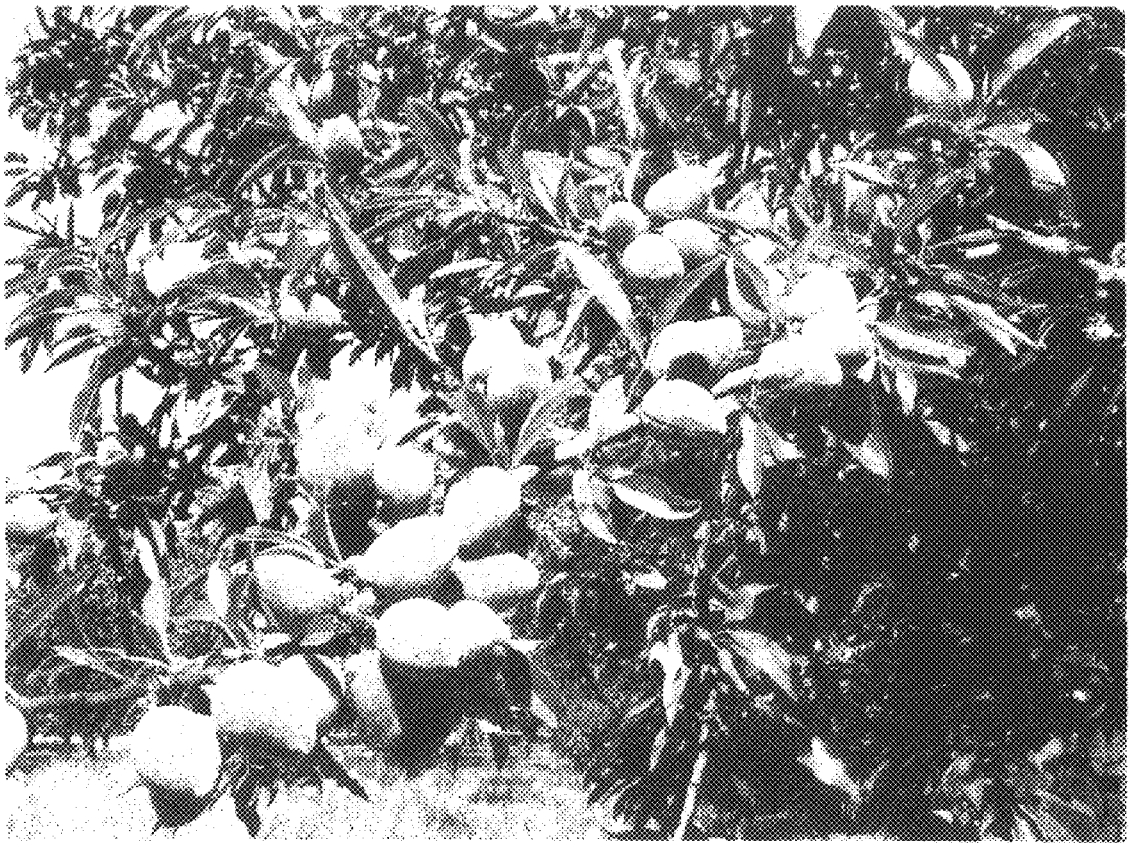
FIG. 2 is a picture of a representative nut set and leaves from the original 'Bluegum' variety of almond tree.
Figure 3:
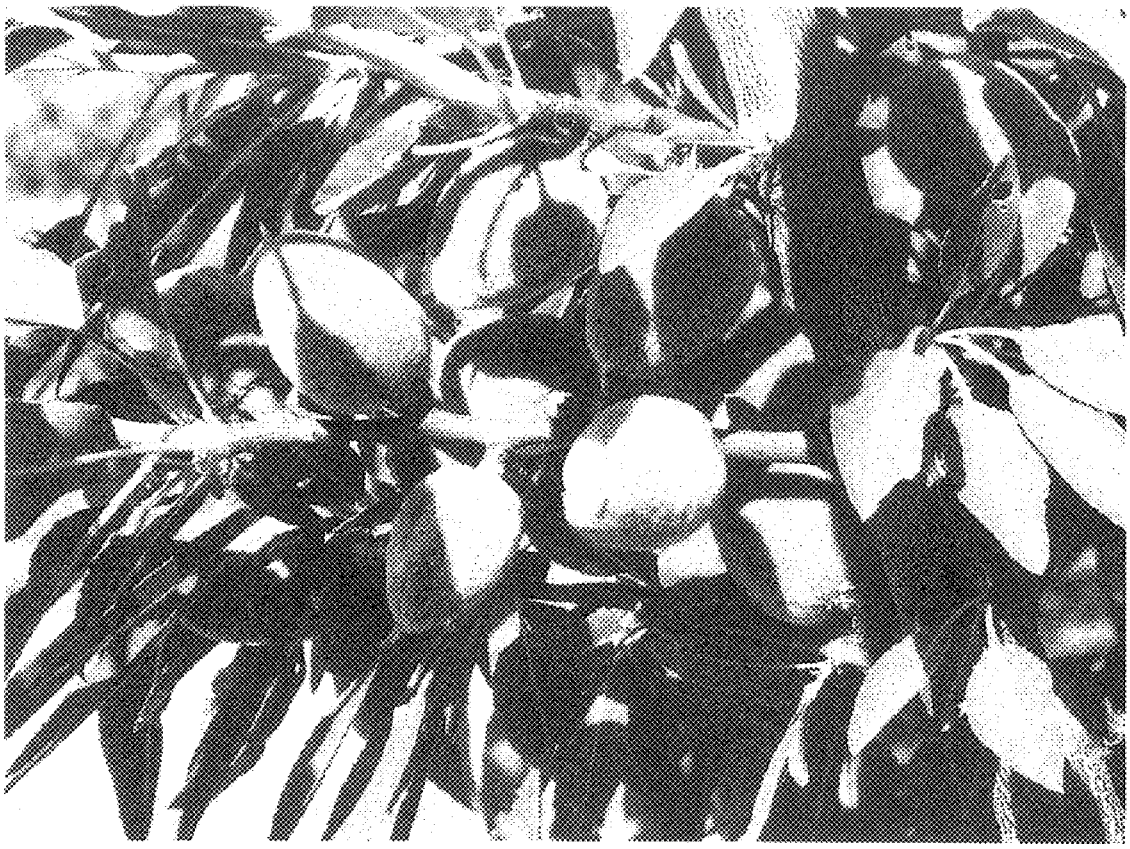
FIG. 3 is a picture of a representative nut set and leaves from one of the progeny trees of the 'Bluegum' variety.
Figure 4:
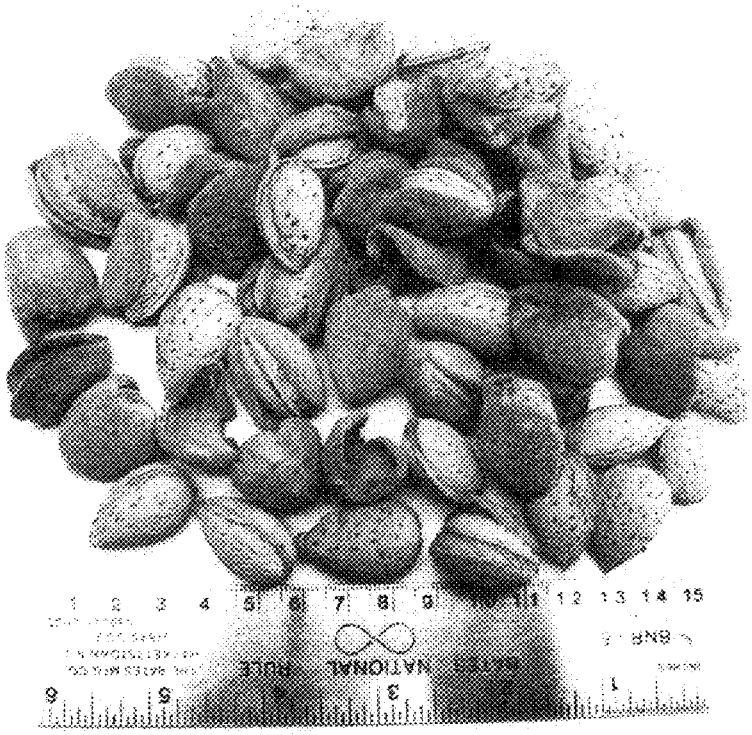
FIG. 4 is a picture of unhulled nuts at harvest produced by the original 'Bluegum' variety of almond tree.
Figure 5:
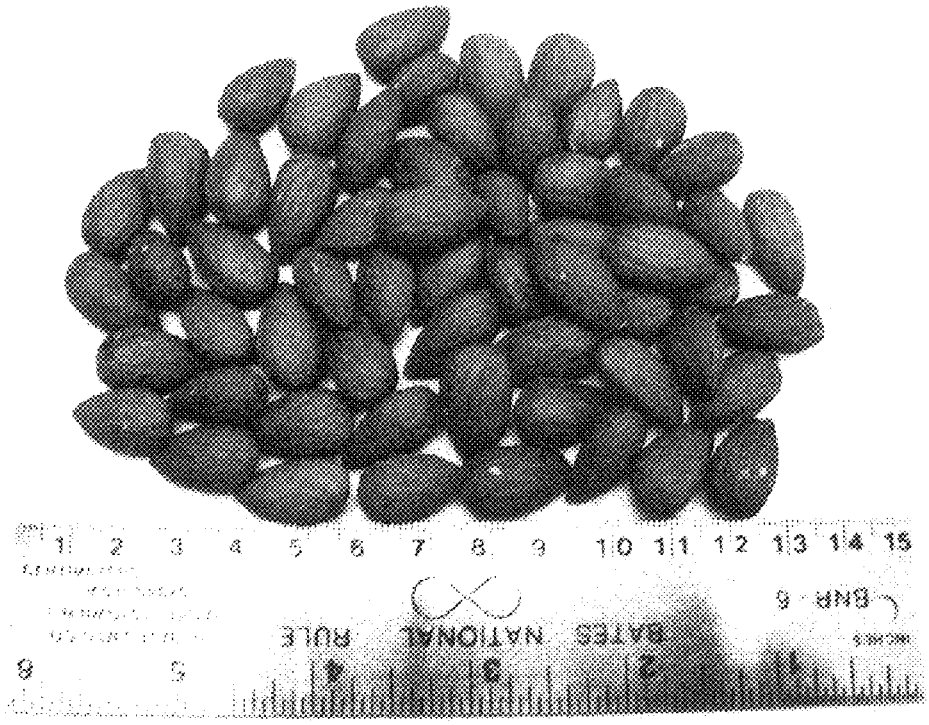
FIG. 5 is a picture of edible nut kernels produced by the original 'Bluegum' variety of almond tree.

It should be noted that colors illustrated in the pictures of FIGS. 1–5 may vary with lighting conditions at the time the original picture was taken.

DETAILED DESCRIPTION

Referring more particularly to the specific taxonomical details of this new and distinct variety of almond tree, the following has been observed under the growing conditions prevailing in Modesto, Calif. Observations were based on the original tree, aged about 17 years, and asexually reproduced progeny, aged about 3 years. The original tree remained growing on its own roots, while progeny were grown on 'Nemaguard' rootstock (unpatented). Any color measurements referenced below by the designation R.H.S. refers to The Royal Horticultural Society color chart determinations.

Tree:

*Generally.*—Size — Medium size with normal spreading canopy. When compared with the 'Nonpareil' variety, the Bluegum almond tree is nearly equal size, with nearly the same growth habit. Limb diameter, branch size, and crotch angles are typical and non-distinctive compared to other almond varieties. Density — Open depending upon pruning practice. Vigor — Better than most pollinators but not excessive. Regularity of bearing — Observed in the original tree to be regular, especially in years in which pollination weather is less than optimum. Fruiting efficiency — Precocious — Starting at second leaf (observed in both the original tree and the progeny), nuts set on spurs, which are two years old, or older, and are predominantly spaced from 2–3 centimeters apart.

Trunk:

*Form.*—Generally — Medium as compared with other common almond cultivars. Trunk diameter of the original tree (aged 17 years) is 12 inches at 24 inches above ground.

*Surface texture.*—Normal almond bark. Young trees have smooth bark, grey brown (RHS 199-B) in color. Older trees have rough bark, grey brown (RHS 199-B) in color. The grey-green stripes of the branches (described below) do not extend to rough, mature bark, such as a mature trunk.

Branches:

*Form.*—Normal as compared with other common almond cultivars.

*Surface.*—Relatively smooth, with distinctive vertical stripes. New shoots are light green (RHS 193-D) with a slight reddish tint (RHS 172-A) on the growing tips and do not exhibit the stripes. Young primary and secondary branches are grey-orange (RHS 172-A), turning to grey-brown (RHS 199-B) with age, with grey-green (RHS 201-D) stripes.

*Form.*—Straight, and having few current year laterals.

*Length.*—Approximately 6 to 30 centimeters per one year of growth (2.5 to about 12 inches).

*Nodes.*—Numbers — approximately 5 to 20 nodes will be found on one year branches.

*Internodes.*—Length — Approximately 1 to 2 centimeters on one year branches.

*Leaf buds.*—Position — Terminal very short and pointed. Lateral buds are smaller and triangular in shape. Occasionally, double leaf buds may be found at the basal end of the shoots.

*Flower buds.*—Generally lateral in position and distinctively plump and elliptical in shape. Pink-white (RHS 55-C) in color, measuring 8 mm wide and 15–20 mm long, at the pink bud stage.

*Scales.*—Generally — Light brown and non-distinctive.

*Spurs.*—Generally — Short and stubby. Often found in clusters spaces 1–1.5 centimeters apart.

*Length.*—Approximately 0.5 to 1 centimeters.

*Numbers.*—2 to 10 lateral buds will normally become flower buds.

*Epidermis.*—Color — Early season spurs are light green turning to light brown as the season progresses.

*Terminal buds.*—Shape — Pointed, small and light brown contrasting with the lateral buds which are less pointed.

*Two-year-old wood.*—Color is generally reddish brown with distinctively colored vertical stripes.

*Three-year-old wood.*—Generally — Color of three-year-old wood has been observed in the original tree only and has been found to be lighter brown to tan. Many peduncles from previous years are intermixed with clusters of new current season flower buds.

*Four year old wood.*—Color of the four year wood has been observed in the original tree only and has been found to be generally tan to silver but not particularly distinctive. Many persistent peduncles are present, often occurring in clusters from which fruit has been produced on previous years.

Leaves:

*Quantity.*—Abundant.

*Shape.*—Long and elliptical, tapering to the apex about ⅓ of the way to the apex.

*Tip.*—Shape — Acuminate, and tapering to a more or less acute angle.

*Color.*—Both the upper and lower surfaces of mature leaves are green (RHS 138-D).

*Base angle.*—Obtuse.

*Size.*—Average length — Approximately 40 to 75 milimeters, and having an average length of 55 milimeters.

*Width.*—Approximately 15 to 25 millimeters having an average width of about 22 millimeters.

*Ratio of petiole length to leaf length.*—Approximately 0.25.

*Ratio of blade width to blade length.*—Approximately 0.3.

*Shoot leaves.*—Generally — Medium to large in size, flat and uniform. Color — Top surface light to dark green (RHS 142-B to 141-C) depending upon leaf maturity. Lower surface lighter green (RHS 142-D). Shoot leaves are emerging new leaves, as opposed to the fully mature leaves described above.

*Marginal leaf form.*—Crenate with shallow crenations.

*Glands.*—Generally — Inconspicuous, or missing.

*Leaf petiole.*—Shape — Cylindrical, tapering through the leaf to the leaf tip. Grooved on the upper side.

*Petiole color.*—Distinctive light green when compared against the darker green leaf blade.

Flowers:

*Date of 10% bloom.*—Approximately Feb. 15, 2000, for the original tree at the inventor's orchard in west Modesto, Calif., and the progeny trees planted in Modesto, Calif.

*Date of full bloom.*—Approximately Feb. 22, 2000, for the original tree at the inventor's orchard in west Modesto, Calif., and the progeny trees planted in Modesto, Calif.

*Bloom.*—Bloom 2000 — The bloom data is distinctive in that it was compiled during a year in which bloom weather was sub-optimal for good pollination and nut set, yet good crops have been observed on the original 'Bluegum' tree and the adjoining 'Nonpareil' variety trees.

*Blossom density and bloom efficiency.*—Generally — Very heavy on 2 and 3 year old wood, bearing in nut clusters interspersed with leaves. One-year-old wood displays very prolific flower bud production, predominantly on fruiting spurs ranging from 6 to 12 inches in length. Buds on fruiting spurs are predominantly flower buds spaced approximately ½ to 1 inch apart with the terminal bud extending current season growth with 12 to 15 leaf nodes and additional undifferentiated buds.

*Flower arrangement.*—Generally — On older wood, many double flowers are produced from the same pedicel. Younger wood produces closely spaced single flowers.

*Bloom time.*—The present variety commences bloom approximately 1 to 2 days ahead of the 'Nonpareil', continues to bloom through the 'Nonpareil' bloom and has been observed to overlap with the 'Carmel' and 'Fritz' varieties in the same geographical location.

*Cold tolerance.*—Bloom is neither more nor less susceptible to frost injury compared to other cultivars blooming at the same time.

*Pollination compatibility.*—The original tree and asexually propagated progeny have been observed to be excellent pollinators for 'Nonpareil.' Also, the original tree was suitable pollinator for 'Carmel' trees growing nearby, and the asexually produced progeny were observed to be a suitable pollinator for 'Fritz' trees. Furthermore, 'Nonpareil' has been observed to be suitable pollinator for both the original tree and the progeny trees. Additionally, 'Fritz' has been found to be a suitable pollinator for the progeny trees and 'Carmel' has been found to be a suitable pollinator for the original tree.

*Petals.*—Number — Generally 5 and occasionally 6 petals may be found.

*Petal overlap.*—The present variety has flowers that slightly overlap at their extended edges at full expansion.

*Size of flowers.*—Flowers are medium sized and showy thereby providing an attraction to bees and other pollinating insects. At full bloom, blossoms are approximately 3 centimeters in diameter.

*Petals.*—Shape — Broadly obovate. Each petal has an obtuse tip at the base.

*Petals.*—Marginal edge — Somewhat undulate.

*Petals.*—Length — Approximately 1.5 to 2 centimeters.

*Petals.*—Color — bright white (whiter than RHS 155-D).

*Sepals.*—Length — 5 to 8 mm.

*Sepals color.*—Brown (RHS 200-D) at the base, extending to light green (192-A) at the top of the page.

*Flower color.*—Pink bud stage — From the sepals brown to green to white to rose pink at the apex of the bud.

*Flower color.*—Full bloom state — The open flower is very light pink at it's base and apex fading to bright white as the flower reaches full extension.

*Stamens.*—Number — approximately 25.

*Pistil.*—Length — Approximately 1 to 1½ centimeters long, and straight. Pubescence is noted on the lower portion of the stile and pistil.

*Pistil, style and stigma.*—Position — Extends nearly to the height of the anther whorl such that the anthers and stigma are approximately at the same level.

Crop:

*Bearing.*—Based on observations of the original tree, considered regular. Alternate production years not observed. Asexually produced progeny, as of the year 2000, are in their second leaf and have produced nuts that have yet to be harvested and tested.

*Harvesting.*—Approximately September 1 to September 10 (the original tree) at the inventors' orchard at Modesto, Calif. Considered mid-season. Beginning (10% hull-split) approximately 5 days after 'Nonpareil' and harvestable (90% hull-split) about 10 days after 'Nonpareil'. Harvests about 15 days ahead of 'Carmel'.

*Productivity.*—Precocious and heavy. Third-leaf progeny trees planted in Kern County, Calif., yielded 7.5 kernel pounds per tree. This yield compares favorably with other varieties of the same age.

*Distribution of nuts.*—Uniform through both old and new wood throughout the original tree.

*Immature nut.*—Shape — The side view of the immature nut is heart-shaped, being round, but tapering to the apex. The nut is very symmetrical tapering to a blunt point.

*Dorsal edge.*—Generally — From the basal end to the apical end the axis follows a distinctively straight and balanced line.

*End view.*—Basal and apical — tight, rounded and compact.

*Base.*—Straight.

*Apex.*—Shape — A blunt, heart-shaped tip having no indentation. In the early season, the style rudiment is readily noticeable. By harvest time the rudiment has sloughed off.

*Peduncle attachment.*—The attachment is medium in size and round in shape. The immature nut is securely fastened to the peduncle but the mature nut separates easily, providing easy harvest.

*Hull surface.*—Generally smooth and even with a fine white-green pubescence (RHS 190-D) evenly distributed over a pale olive-green (RHS 193-B) nut.

*Surface testure.*—Abundant, short pubescence. The surface is even and smooth with no grooves or hull undulations.

*Dehiscence.*—Both the progeny and the original tree have a dorsal suture that is very shallow but distinct before dehiscence. Generally, as observed in the original tree, the immature nut dehisces only on the ventral side and many nuts fall clean from the hull. Nut abscission has been observed to be complete for nuts from the original tree.

*Mature nut.*—Generally — Considered a well sealed soft shell variety facilitating easy hulling and shelling while providing protection from easy insect entry. The shelled nut color is distinctive in that it is an attractive light brown (RHS 173-C).

*Size.*—Generally, as observed for both the progeny tree and the original tree — Medium as compared to other varieties. The nuts are generally smaller and plumper than the 'Nonpareil' variety. The shelled nut color is distinctive in that it is an attractive chocolate brown.

*Shape.*—Side — Heart-shaped. End — oval to round.

*Ventral edge.*—Shape — Sharply and uniformly curved from base to tip.

*Dorsal edge.*—Shape — Gently and uniformly curved from base to tip.

*Wing.*—A very thin and short but noticeable wing extends from the base to the tip. It is considered very narrow in relative comparison to other varieties.

*Base scar.*—Shape — Oval and flat.

*Apex.*—Shape — Having a sharp and acute tip.

*Surface.*—Color —Light brownish tan.

*Surface texture.*—Very smooth but with numerous pits evenly distributed over the outer cork.

*Shelling percentage.*—*Approximately* 60%.

*Kernel.*—Length — Approximately 21.5 millimeters.

*Width.*—Approximately 12.5 millimeters.

*Thickness.*—Approximately 10 millimeters.

*Kernel.*—The side view of the kernel appears heart-shaped. Both the ventral and the dorsal sizes uniformly slope to the apex. The broadest portion of the kernel is one-third the distance from the basal end to the apex.

*Ventral edge.*—Shape — Very square shoulder between the basal end scar and the sloping ventral line to the apex.

*Dorsal edge.*—Gently curving dorsal line from base scar to apex. Distinctively different from the square cornered ventral edge.

*Base scar.*—Round and oval, not prominently noticeable.

*Basal end view.*—Oval.

*Pellicle.*—Color — Light brown (RHS 173-C). Distinctively uniform without lines or veins. The surface is smooth and not wrinkled.

*Surface texture.*—No noticeable surface pubescence.

*Double kernels.*—Numbers — Very low. 0–2 percent in the 1998 to 1999 samples evaluated.

*Flavor.*—Exceptional mild to slightly sweet flavor. No off flavors or aftertaste. No hint of almond bitterness.

*Quality.*—Determined to be marketable under the 'California' almond classification. Blanchable. Pest tolerance is comparable to other California soft-shelled varieties and as such will require normal monitoring.

Although this new variety of almond tree possesses the described characteristics described above, as a result of the growing conditions prevailing in the central part of the San Joaquin Valley of central California (specifically west Modesto), it should be understood that variations of the usual magnitude and characteristics incident to changes in growing location, climatic conditions, and management practice may affect the observations. In addition, color is expected to vary somewhat with growing conditions and the lighting conditions prevalent at the time color observations are made.

We claim:

1. A new and distinct variety of almond tree substantially as herein shown and described characterized particularly as to novelty by its ability to pollinate in the early season.

* * * * *

UNITED STATES PATENT AND TRADEMARK OFFICE

CERTIFICATE OF CORRECTION

PATENT NO. : PP 12,737 P2
DATED : July 2, 2002
INVENTOR(S) : Flora et al.

It is certified that error appears in the above-identified patent and that said Letters Patent is hereby corrected as shown below:

Title page,
DESCRIPTION,
Line 37, change the word "almomds" to -- almonds --

Column 3,
Line 28, change "Open depending" to -- Open, depending --

Column 7,
Lines 2-4, delete "The shelled nut color is distinctive in that it is an attractive chocolate brown."

Signed and Sealed this

Fourteenth Day of October, 2003

JAMES E. ROGAN
*Director of the United States Patent and Trademark Office*